US00PP33299P2

(12) United States Plant Patent
Bak et al.

(10) Patent No.: US PP33,299 P2
(45) Date of Patent: Jul. 27, 2021

(54) ***TILLANDSIA* PLANT NAMED 'ZIVA'**

(50) Latin Name: ***Tillandsia* sp.**
Varietal Denomination: Ziva

(71) Applicant: Corn Bak B.V., Assendelft (NL)

(72) Inventors: Elly Bak, Rijsenhout (NL); Nicolaas D. M. Steur, Oude Niedorp (NL)

(73) Assignee: Corn Bak B.V.

( * ) Notice: Subject to any disclaimer, the term of this patent is extended or adjusted under 35 U.S.C. 154(b) by 0 days.

(21) Appl. No.: 16/952,628

(22) Filed: Nov. 19, 2020

(51) Int. Cl.
*A01H 5/02* (2018.01)
*A01H 6/22* (2018.01)

(52) U.S. Cl.
USPC ..... Plt./370
CPC ..... *A01H 6/22* (2018.05)

(58) Field of Classification Search
USPC ..... Plt./370
CPC ..... A01H 6/22
See application file for complete search history.

(56) References Cited

PUBLICATIONS

UPOV hit on a *Tillandsia* plant named, 'Ziva', QZ PBR 20202332, filed Sep. 24, 2020.*

* cited by examiner

*Primary Examiner* — Anne Marie Grunberg
(74) *Attorney, Agent, or Firm* — Cassandra Bright

(57) ABSTRACT

A new and distinct *Tillandsia* hybrid plant named 'Ziva' characterized by solid growth habit; funnel-form rosette plant, measuring about 30 cm in height (above the pot when flowering); numerous, green color foliage, measuring about 47 cm in length and about 5 cm in width; abundant floral bract production; bracts have a unique pinkish red inflorescence (RHS 50A); panicle inflorescence, measuring about 28 cm in height (flowering part) and about 15 cm in diameter; and long-lasting habit.

2 Drawing Sheets

Latin name of the genus and species of the claimed plant: *Tillandsia* sp.

Variety denomination: 'Ziva'.

BACKGROUND OF THE INVENTION

The present invention relates to a new and distinct hybrid cultivar of *Tillandsia* plant, botanically known as *Tillandsia* sp., of the family Bromeliaceae, and hereinafter referred to as 'Ziva'

The new *Tillandsia* 'Ziva' originated from a cross made in a controlled breeding program by the inventors in 1996. The female or seed parent is the unnamed and unidentified *Tillandsia* selection identified by code 9601090007 (unpatented). The male or pollen parent is the unnamed *Tillandsia* selection identified by code 9601090055 (unpatented). The new *Tillandsia* 'Ziva' was discovered and selected by the inventors in 2000 as a single flowering plant within the progeny of the stated cross in a controlled environment in Assendelft, The Netherlands.

Asexual reproduction of the new *Tillandsia* cultivar was first performed by off-shoots beginning in 2008 and then by tissue culture beginning in 2016 in Assendelft, The Netherlands. The new cultivar reproduces true to type.

Methods for cultivation and crossing of *Tillandsia* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag, Paul Parey, Berlin (1986); and Rauh, Werner, BROMELIEN, Verlag Eugen Ulmer, Stuttgart (1981).

BRIEF SUMMARY OF THE INVENTION

The following traits have been repeatedly observed and are determined to be unique characteristics of 'Ziva' which in combination distinguish this *Tillandsia* as a new and distinct cultivar:

1. Solid growth habit;
2. Funnel-form rosette plant, measuring about 30 cm in height (above the pot when flowering);
3. Numerous, green color foliage, measuring about 47 cm in length and about 5 cm in width;
4. Erect, compound panicle shape, pinkish red (RHS 50A) inflorescence, measuring from about 28 cm in height and about 15 cm in diameter;
7. Long-lasting habit.

Plants of the parental cultivars, *Tillandsia* selection identified by code 9601090007 and *Tillandsia* selection identified by code 9601090055 (both unpatented) are no longer available to provide a botanical comparison with the new *Tillandsia* hybrid 'Ziva'.

The inventors are not aware of comparable cultivars in the *Tillandsia* Genus.

However, one can make a comparison to 'T1072', having U.S. Plant Pat. No. 29,755. The instant plant differs from 'T1072' in plant spread and bract coloration. 'Ziva' is approximately twice as tall and wide as the comparator plant and has pink-reddish bracts compared to the red-purple bracts of 'T1072'.

BRIEF DESCRIPTION OF THE PHOTOGRAPH

The accompanying photograph illustrates the overall appearance of the new *Tillandsia* cultivar 'Ziva' showing the colors as true as is reasonably possible with colored reproductions of this type. Colors in the photograph may differ slightly from the color values cited in the detailed botanical description which accurately describes the color of 'Ziva'.

DETAILED BOTANICAL DESCRIPTION

Figure 1:
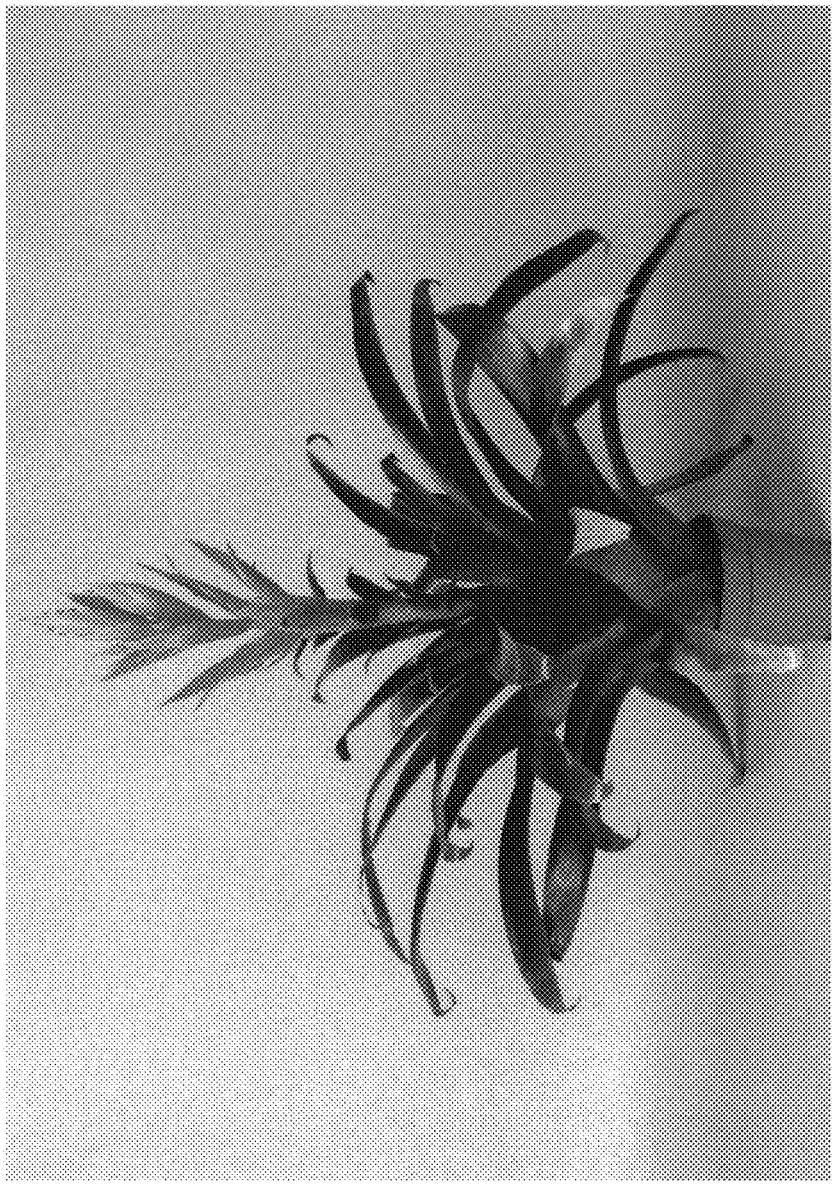
FIG. 1 shows a side perspective view of a typical potted flowering plant of 'Ziva' at about 13 months of age from potting.
Figure 2:
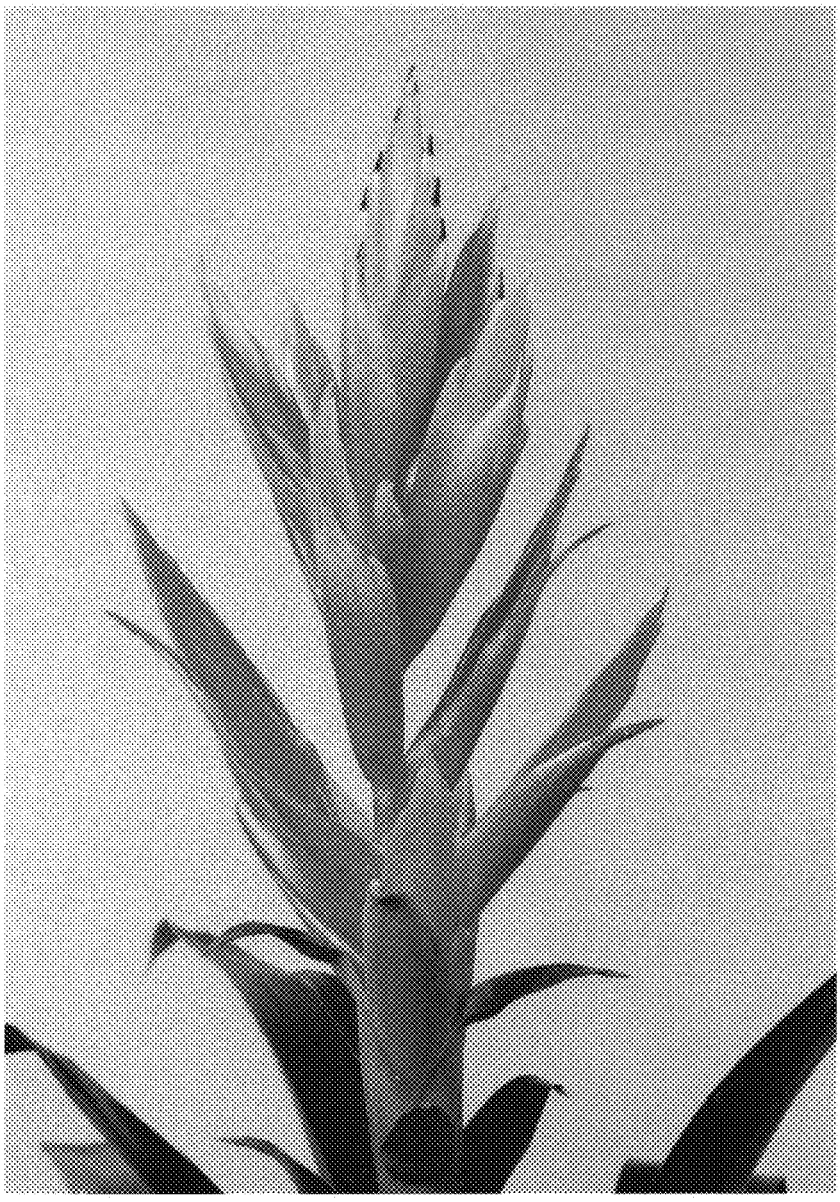
FIG. 2 shows a close-up top view perspective of the inflorescence and top bracts produced by a typical potted, flowering plant of 'Ziva', at 13 months of age from potting size.

'Ziva' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant.

For example, substantial differences in plant height and diameter, number of leaves, can result depending on the size of the plant at the time that flowering is induced by flowering treatment. Since treatment to induce flowering disrupts normal watering and fertilization regimens, flowering treatment of relatively smaller plants adversely affects the growth of the plant.

The aforementioned photographs, together with the following observations, measurements and values describe the new *Tillandsia* 'Ziva' as grown in a greenhouse in Assendelft, The Netherlands, under conditions which closely approximate those generally used in commercial practice. Plants of 'Ziva' were grown in a greenhouse with day temperatures ranging from 20° C. to 28° C. and night temperatures ranging from 18° C. to 23° C. No artificial lighting or photoperiodic treatments were conducted, but plants of 'Ziva' are forced into flowering. The following fertilizer is added when growing plants of 'Ziva': 1 part nitrogen, 0.6 parts phosphor, 2 parts Kalium and 0.1 parts magnesium.

Color references are made to The Royal Horticultural Society Colour Chart (R.H.S.), 2001 edition, except where general colors of ordinary significance are used. Color values were taken under daylight conditions in a greenhouse in Assendelft, The Netherlands. The age of the plants of 'Ziva' described is about 18 weeks after flowering treatment.

Plant:

- *General appearance and form*.—Height: About 30 cm (when flowering). Width: About 75 cm. Shape: Funnel form rosette.
- *Growth habit*.—Single rosette.
- *Plant vigor*.—Good.
- *Flowering season*.—A fully grown plant can flower year-round, starting about 18 weeks after induction of natural light or through flowering treatment.
- *Cold tolerance*.—Frost tender. Temperatures below 5° C. may damage plants.
- *Fragrance*.—None.

Foliage:

- *Quantity*.—About 32 (depending on the size of the plant).
- *Size of leaf*.—Length: About 47 cm (when flowering). Width: About 5 cm.
- *Overall shape*.—Linear-lanceolate.
- *Apex shape*.—Acuminate.
- *Base shape*.—Strap-like around central axis.
- *Margin*.—Entire.
- *Texture*.—Smooth (both surfaces).
- *Orientation*.—Leaf blades arch continuously from base.
- *Color*.—Leaf color can vary somewhat depending on growing conditions. Mature and immature: Upper surface: green, RHS 147A. Under surface: green, RHS 146A.
- *Venation*.—None.

Inflorescence:

- *Borne*.—Erect stalks.
- *Shape*.—panicle.
- *Size*.—Length: About 55 cm, flowering part about 28 cm. Diameter: About 15 cm.
- *Color*.—Pinkish red, closest to RHS 50A.
- *Petals*.—hidden behind the floral bracts.
- *Number*.—3 per flower.
- *Length*.—About 5 cm.
- *Width*.—About 0.6 cm.
- *Overall shape*.—Ligulate.
- *Apex shape*.—Obtuse.
- *Base shape*.—Fused.
- *Color*.—Upper and Under surfaces: yellow, closest to RHS 8B.
- *Sepals*.—Hidden behind the floral bracts. Number: 3 per flower. Length: About 3.5 cm. Width: About 1.0 cm. Overall Shape: Ligulate. Apex Shape: Acute. Base Shape: Fused. Color: Yellow-white, closest to RHS 158D.
- *Bracts*.—Scape bracts: Quantity: about 12. Arrangement: Alternate. Size: Length: about 20 cm (lowest) to about 11 cm (scape bracts positioned just below the primary bracts). Width: About 4 cm. Overall shape: Lanceolate. Apex shape: Acuminate. Base shape: Fused. Margin: Entire. Texture: Smooth. Color: Upper surface: yellow-green (closest to RHS 146A) with pinkish red (closest to RHS 39B). Under surface: yellow-green (closest to RHS 146A) with pinkish red (closest to RHS 39B).
- *Primary bracts*.—Quantity: About 12. Arrangement: Alternate. Size: Length: About 7.5 cm to 11 cm. Width: About 3 cm. Overall shape: Lanceolate. Apex shape: Acute. Base shape: Fused. Margin: Entire. Texture: Smooth. Color: Upper and under surfaces: Pinkish red, closest to RHS 39A.
- *Floral bracts*.—Disposed within the inflorescence. Quantity: About 64. Size: Length: About 6 cm. Width: About 3 cm (folded double in length). Overall shape: Lanceolate. Apex shape: Acute. Base shape: Fused. Margin: Entire. Texture: Smooth. Color: Upper and under surfaces: pinkish red, closest to RHS 50A.

Reproductive organs:

- *Androecium*.—Stamen: Number: 6 per flower. Length: About 3 cm. Diameter: About 0.1 mm. Color: yellow, closest to RHS 8B. Anther: Length: About 0.7 cm. Color: yellow, closest to RHS 13B. Pollen: None.
- *Gynoecium*.—Pistil: Number: 1 per flower. Length: About 3 cm. Stigma: Shape: 3-parted. Width: About 0.2 cm. Color: greyed-orange, closest to RHS 165 C. Style: Length: About 4 cm. Color: yellow, closest to RHS 8D. Ovary: Position: Superior. Shape: Conical. Length: About 0.7 cm. Diameter: About 0.4 cm.

Other characteristics:

*Seeds/fruit*.—Sterile hybrid, no seed or fruit produced.

*Disease/pest resistance and susceptibility*.—Neither resistance nor susceptibility to common diseases and pests of *Tillandsia* observed.

We claim:

1. A new and distinct *Tillandsia* hybrid plant named 'Ziva', substantially as illustrated and described herein.

* * * * *